United States Patent [19]

Rajadhyaksha et al.

[11] 4,006,204
[45] Feb. 1, 1977

[54] PHOSPHORIC ACID DIESTERS

[75] Inventors: Vithal J. Rajadhyaksha, Mission Viejo; James V. Peck, Newport Beach; William D. Fairbairn, Atherton, all of Calif.

[73] Assignee: Nelson Research & Development Company, Irvine, Calif.

[22] Filed: Apr. 30, 1975

[21] Appl. No.: 572,888

[52] U.S. Cl. .............................. 260/958; 260/247; 260/326.61; 260/924; 260/925; 260/945; 260/951; 260/954; 260/955; 260/961; 260/963; 260/964; 424/199; 424/200; 424/211; 424/217; 424/218; 424/222; 424/224; 424/225

[51] Int. Cl.² ...................... C07F 9/12; C07F 9/09; C07F 9/40

[58] Field of Search .......... 260/958, 961, 963, 964, 260/925

[56] References Cited

UNITED STATES PATENTS

| | | | |
|---|---|---|---|
| 2,329,707 | 9/1943 | Farrington et al. | 260/958 X |
| 2,872,351 | 2/1959 | Wedell | 260/958 X |
| 3,268,629 | 8/1966 | Cherbuliez et al. | 260/961 X |
| 3,851,019 | 11/1974 | Hogberg et al. | 260/946 |
| 3,862,270 | 1/1975 | Hogberg et al. | 260/946 |
| 3,869,527 | 3/1975 | Hogberg et al. | 260/946 |

OTHER PUBLICATIONS

Houben–Weyl, Methoden der Organischen Chemie, 12/2, (1963), pp. 258 and 259.

*Primary Examiner*—Richard L. Raymond
*Attorney, Agent, or Firm*—Martin A. Voet

[57] ABSTRACT

The invention relates to compounds represented by the following general structure:

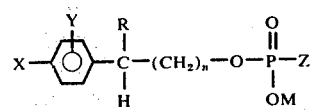

and their method of making. These compounds are therapeutically useful as anti-inflammatory agents and operate as inhibitors of prostaglandin synthetase and also as prostaglandin receptor blockers.

8 Claims, No Drawings

PHOSPHORIC ACID DIESTERS

BACKGROUND OF THE INVENTION

1. Field of the Invention

This invention generally relates to esters of phosphoric and phosphonic acids and their method of making. More particularly, this invention relates to diesters of phosphoric acid and monoesters of phosphonic acids in which one of the groups involved in the ester formation is derived from α-(3,4-disubstituted phenyl) alkanols.

2. Background of the Prior Art

The development of anti-inflammatory compounds in the past two and a half decades has been the growth of a great many new drugs. Most of these have been steroids of 11-oxygenated pregnane series and derivatives of aryl acetic acids. Many of these compounds, while highly effective, have the drawback of causing many side effects. There has been a long-felt need for effective, non-steroidal anti-inflammatory compounds of much simpler structure and having fewer side effects.

For example, both enantiomers of compounds having the structural formula

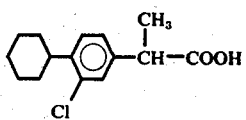

are known to possess anti-inflammatory properties (U.S. Pat. No. 3,435,075). However, this compound is also toxic and therefore is not useful in the treatment of inflammation. Other phenyl acetic acid derivatives, such as, for example, Ibuprofen and Flurbiprofen are also known to possess anti-inflammatory activity.

SUMMARY OF THE INVENTION

The esters of phosphoric and phosphonic acids prepared by the methods described herein are anti-inflammatory agents. These compounds have a high degree of anti-inflammatory activity and are effective in the treatment of arthritic and dermatological disorders and in like conditions which are responsive to treatment with anti-inflammatory agents, that is, they act to temporarily alleviate the signs and symbols of the foregoing conditions.

The present invention relates to compounds having the general structure:

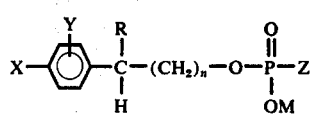

wherein X is an alkyl group having 1-12 carbon atoms, aryl, substituted aryl, cycloalkyl e.g. cyclohexyl or cyclopentyl or a heterocyclic ring system such as pyrrolidinyl, Δ³-pyrrolinyl, morpholinyl, etc.

Y is either hydrogen or halogen, such as, for example, fluorine, chlorine or bromine and preferably fluorine or chlorine: R is lower alkyl and preferably methyl; n is 0 or 1, and Z is selected from the group consisting of an alkyl group having 1-12 carbon atoms, aryl, substituted aryl, aralkyl, substituted aralkyl, —O-alkyl, where the alkyl group has 1-12 carbon atoms, —O-aryl or substituted —O-aryl.

The substituents on aryl rings may be halogen, nitro, $CF_3$, lower alkyl, lower alkoxy or di-lower alkylamino.

M is hydrogen, an alkali metal salt, an amine salt or lower alkyl group and preferably methyl.

The following examples illustrate some of the compounds covered by the general formula above:

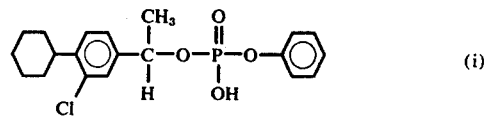 (i)

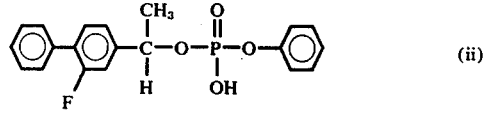 (ii)

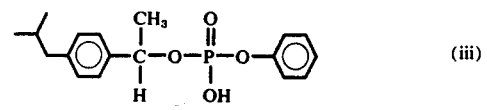 (iii)

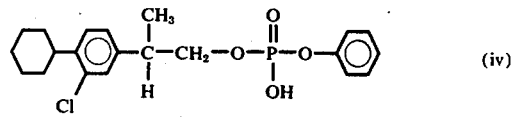 (iv)

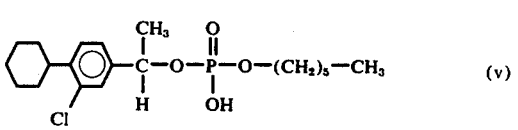 (v)

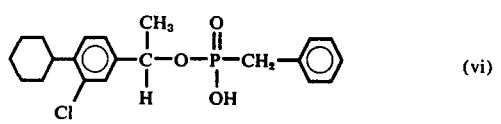 (vi)

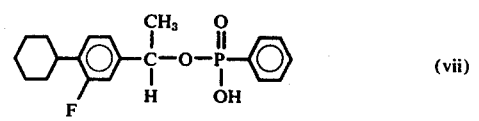 (vii)

and pharmaceutically acceptable salts thereof.

These compounds are useful broadly in the treatment of inflammation such as dermatitis, uveitis, arthritis, sunburn, etc. By "treatment of inflammation" is meant the temporary alleviation of symptoms of inflammation.

The 4-substituted α-(3-halophenyl) alkanols are prepared in general by methods as described in U.S. Pat. No. 3,435,075. The alkanols are resolved by known chemical techniques before converting them into the phosphate or phosphonate esters. Optically active alkanols may also be obtained by reduction of alkyl ketones, obtained as intermediates in the preparation of racemic alkanols with enzymes or micoorganisms or by asymmetric reduction.

Phosphate diesters of this invention can be prepared by methods described in Houben-Weyl's "Methoden der Organischen Chemie", Band XII, Teil II, p. 226; the heading "Phosphorylation" by D. M. Brown, p. 75, in "Advances in Organic Chemistry" Vol. 3, Interscience Publishers, 1963 and E. Cherbulier in "Chemistry of Phosphorous Compounds" Vol. 6, Chapter 15, Wiley-Interscience, Ed. G. M. Kosalapof and L. Maier, 1972.

Phosphonate esters of this invention can be prepared by methods described in Houben-Weyl's "Methoden der Organischen Chemie", Band XII, Teil I.

For example, P,P-diphenyl pyrophosphoric acid in the form of its pyridinium salt may be used as the phosphorylating agent. It is prepared by any of the conventional methods mentioned in reference 1, p. 880. Phosphorylation of an alkanol with P,P-diphenylpyrophosphate is carried out in presence of a condensing agent preferentially in a basic solvent such as pyridine. The condensing agent of choice is trichloroacetonitrile. The reaction is carried out preferentially at about 70° C for about 18 hours.

Another method of preparing the phosphate diester is to condense an alkyl phosphoric acid or an aryl phosphoric acid in an activated form with an excess of alkanol. Activating agents for this reaction are p-toluene sulfonic acid, s-triazine trichloride, ethoxyacetylene dicyclohexylcarbodiimide, trichloroacetonitrile, and carbonyldiimidazole. The latter three are preferentially used. The reaction is carried out in presence of a tertiary base such as pyridine at 90° C. Any pyrophosphoric acid derivative formed is removed as cyclohexylamine salt at 0° C and then the diester is isolated from the filtrate by addition of petroleum ether.

Alternatively the primary phosphoric acid ester, such as an aryl or an alkyl phosphoric acid is allowed to react in an activated form with about one mole of an alkanol. This reaction may, for instance, be carried out in the presence of about two moles of 2,4,6-triisopropylbenzene sulfonyl chloride and about 2 moles of tertiary amine, e.g. triethylamine, using a suitable solvent, for instance pyridine. After the condensation has been completed, water is added, making it possible to isolate the phosphoric acid diester.

Yet in another method an alkanol is treated with an aryl or an alkyldichlorophosphate in presence of a tertiary base such as pyridine or diisopropylethylamine followed by hydrolysis of the phosphate diester monochloride. Yet in another method the silver salt of an arylbenzylphosphate or alkylbenzylphosphate is treated with alkyl bromide prepared from the corresponding alkanol by conventional methods. The triester so obtained is subjected to hydrogenolysis or hydrolysis with a base or a neutral salt and affords the phosphate diester of this invention.

Yet in another method, especially for the preparation of dialkyl phosphates, a monoalkyl phosphate is dissolved in methanolic tetramethylaminium hydroxide and the quaternary aminium salt is isolated by removing solvent in vacuum at 40°. Subsequent reaction with one mole of an alkyl halide is carried out in acetonitrile, the time depending on the reactivity of the halide. The reaction is carried out, especially if alkyl chlorides are used, in boiling acetonitrile for a period of up to 50 hours. When the dialkyl hydrogen phosphate is a solid, it can be readily purified by recrystallization, otherwise it can be converted to the sodium salt by neutralization in alcohol, which procedure simultaneously removes the unreacted monoalkyl phosphate as the insoluble disodium salt.

For the preparation of phosphonate monoesters, represented by the formulae VI and VII, aryl or aralkylphosphonic dihalide is treated with an equimolar amount of an alkanol in presence of a tertiary base such as pyridine or trimethylamine. The aryl- or aralkylphosphonic acid alkyl ester halide is then hydrolyzed to the phosphonate monoester. The hydrolysis is carried out in hot water or in aqueous alkali, whereupon an alkali salt of the monoester is obtained which on acidifying gives the free monoester.

Yet in another method, an aryl- or aralkylphosphonic acid dialkylester is hydrolyzed in presence of a mineral acid or an alkali. Alkaline hydrolysis, is, however, preferred. The hydrolysis can be carried out with aqueous sodium hydroxy, aq. barium hydroxide or alcoholic alkali. The starting diester can be prepared from aryl- or aralkylphosphonic dihalide with an alkanol in the presence of a base such as pyridine.

Yet in another method, an alkanol is refluxed with, for example, P,P-arylpyrophosphonic acid prepared in situ from an arylphosphonic acid and dicyclohexylcarbodiimide. The reaction is conveniently carried out in tetrahydrofuran for 10 to 24 hours.

Yet in another method, aryl- or aralkylphosphonic acid alkylbenzyldiester is treated with Pd/Hydrogen to obtain the phosphonate monoester. The diesters can be prepared according to the references mentioned before.

The active compounds described herein may be used in the form of pharmaceutical compositions.

The pharmaceutical compositions may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate or stearic acid. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with an oil medium, for example arachis oil, liquid paraffin or olive oil.

Aqueous suspensions contain the active ingredients in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile, injectable aqueous suspension. This suspension may be formulated according to the known art using those suitable dispersing or wetting agents and suspending agents which have been mentioned above. The sterile injectable preparation may also be a sterile, injectable solution or suspension in a non-toxic parenterally-acceptable diluent or solvent, for example as a solution in 1,3-butane diol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 10 mg and about 500 mg of the active ingredient of the formula stated above.

The pharmaceutical compositions may be in the form suitable for topical use, for example, being used together with conventional pharmaceutically acceptable topical carriers including, but not limited to ointments, aqueous solutions, aerosols, suspensions or oil solutions. The proportion of the active compound in the composition may be widely varied. It is only necessary that the active ingredient of the invention be present in the carrier in sufficient concentration such that a conventional topical dosage form contains an effective amount of active compound.

The manner of application of the foregoing formulations is generally conventional: one to four times daily application of the topical formulation to the inflamed area by spraying or coating the inflamed area with a conventional amount of the selected topical formulation. The concentration of active compound which is to be used in the topical formulation ranges from about 0.1 to about 5% and preferably about 0.5 to about 3% by weight.

The foregoing compositions may be used in the topical treatment of inflammation whereby some or all of the signs and symptoms of inflammation are at least temporarily diminished or alleviated by topical application. Examples of conditions to which the foregoing is applicable are sunburn, arthritis, eczema, dermatitis, uveitis, etc.

From the foregoing formulation discussion, it is apparent that the compositions of this invention can be administered topically, orally or parenterally. The term "parenteral" as used herein includes subcutaneous injection, intravenous, intramuscular, or intrasternal injection of infusion techniques.

This invention is further demonstrated by the following examples in which all parts are by weight.

EXAMPLE I

Method of making (±)-α-(3-chloro-4-cyclohexyl phenyl) ethyl phenyl hydrogen phosphate monosodium salt

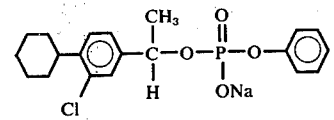

3.31 g (0.0454) mole of dimethyl formamide is added to 9.56 g (0.0454 mole) phenyl dichlorophosphate dropwise. After 5 minutes a yellow paste is formed. To this is added at room temperature a solution of 7.9 g (0.0454 mole) phenyl phosphoric acid, 4.58 g (0.0454 mole) of triethylamine and 30 ml of acetonitrile. After completion of addition (15 min.), the mixture is stirred at room temperature for 3 hours. The solution is filtered to remove triethylamine hydrochloride and 5 ml of water and 10 ml of pyridine is added to the clear yellow solution. This is swirled for a few minutes and then concentrated to a yellow oil. This oil is then completely dissolved in acetonitrile and a solution of 3.9 g (0.092 mole) of lithium chloride in a minimum amount of water is added. A large amount of lithium salt of p,p-diphenyl pyrophosphoric acid precipitates out. This is washed with acetone, then filtered and dried to obtain 10.5 g (67%) of the dilithium salt.

19 g of this material (0.0552 M) is dissolved in 150 ml of water and passed through an Amberlite IR-120 H$^+$ column cooled below 5°, and run into 20 ml of pyridine. The solution is concentrated under reduced pressure and the residual water is azeotroped off with p-dioxane leaving a light yellow oil which solidifies on scratching under pyridine:ether (2:1) to give 22 g (81%) of dipyridinium salt.

1.2 g (0.00245 mole) of the dipyridinium salt of p,p-diphenyl pyrophosphoric acid is combined with 1.46 g (0.006125 mole) of (±)-α-(3-chloro-4-cyclohexylphenyl) ethyl alcohol and 2.45 ml (0.0245 mole) of trichloroacetonitrile, along with 25 ml pyridine. This mixture was stirred at 70° for 18 hours and then concentrated to a dark brown oil. This was dissolved in acetone and an excess of cyclohexylamine was added. A white solid precipitates which is filtered and washed with acetone. The solid is suspended in water and the pH of the solution is adjusted to pH 2. The free phosphoric acid derivative is extracted into chloroform. The organic phase is washed with water, filtered through celite, dried and concentrated to obtain 570 mg (29% based on the pyridinium salt of p,p-diphenylpyrophosphoric acid) of a light yellow oil. This is dissolved in methanol and brought to pH 6.9 with methanolic sodium hydroxide solution. This is then concentrated to an oil, and washed with isopropyl ether. Dissolution results and within 2 days a white powder is isolated out of solution. The following physical characteristics were observed (data taken on free phosphoric acid):

I.R.: 2926, 2858, 1593, 1492, 1449, 1410, 1378, 1212, 1020, 985, 940, 758, 687 cms$^{-1}$.

NMR (CDCl$_3$): 121 δ Singlet
7.0 – 7.35 δ Multiplet
5.4 δ Quintuplet
0.8 – 3.2 δ Multiplet

EXAMPLE II

Method of making (±)-β-(3-chloro-4-cyclohexyl phenyl) propanol phenyl hydrogen phosphate monosodium salt

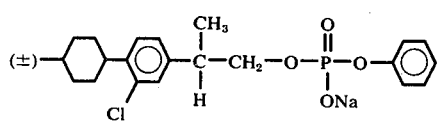

(±)-β-(3-chloro-4-cyclohexylphenyl) ethanol was converted to its cyanide through the bromide by the method shown in U.S. Pat. No. 3,435,075. The hydrolysis procedure to produce the acid was modified as follows:

21.7 g (0.0876M) (±)-1-(3-chloro-4-cyclohexylphenyl)-1-cyano ethane was combined with 60 ml 50% sulfuric acid and heated to 110° for 1 day. The mixture was cooled and the organic material taken up in chloroform. The organic solution was washed twice with water, dried, and concentrated to an oil which was distilled at 160°–180°/50 μ to give 15 g (64%) of a faint yellow clear glass.

12 g (0.045M) (±)-2-(3-chloro-4-cyclohexylphenyl) propanoic acid was dissolved in dry ether (200 ml) and added dropwise, under nitrogen, to a suspension of 2.165 g (0.0698 M) lithium aluminum hydride in 100 ml dry ether. Foaming and warming was observed as the addition was continued for 1 hour, and then the mixture was let stir 3 hours. In succession, 2.5 ml water, 2.5 ml 15% NaOH, and 8 ml water were added. After stirring 10 min., the precipitate was filtered off. The filtrate was dried, concentrated and run through a short silica gel/ethyl acetate column to rid the product of impurities which adhere to silica gel. Concentration of the appropriate fractions gave 10.6 g (93%) of a white cloudy oil.

5.02 g (0.0199 M) (±)-2-(3-chloro-4-cyclohexylphenyl) propyl alcohol was mixed with 3.9 g (0.00797 M) of the dipyridinium salt of p,p-diphenyl pyrophosphoric acid, 11.52 g (0.0798M) trichloroacetonitrile and 40 ml pyridine and the mixture stirred with the exclusion of moisture for 18 hours at 70°–80°. Most of the pyridine was removed under reduced pressure and the brown oil taken up in 0.1N NaOH/ether. The aqueous phase was separated and again washed with ether. The aqueous phase was then acidified and extracted with chloroform. Drying and concentration of the organic solution gave a light yellow oil which solidified. This was dissolved in methanol and adjusted to pH 7 with methanolic NaOH. The solution was concentrated and the resultant oil washed with ether to give 4.1 g (60%) of the sodium salt, a white powder, having the following physical characteristics (data taken on free phosphoric acid):

I.R.: (neat, cm$^{-1}$) 2937, 2858, 1594, 1558, 1492, 1451, 1411, 1391, 1373, 1337, 1210, 1168, 1141, 1020, 1050, 1002, 950, 908, 882, 843, 827, 810, 763, 691, 618.

NMR: 12.3 δ Singlet; 6.9 – 7.6 δ Multiplet; 4.17 δ Triplet; 2.7 – 3.3 δ Multiplet; 0.8 – 2.3 δ Multiplet.

EXAMPLE III

The following compounds were tested for their biological activity in blocking prostaglandin receptor activity. This test is useful in that many kinds of inflammation are at least partially prostaglandin mediated. The structure of the numbered compounds is shown in Table 2. Table 1 below tabulates the results.

Table 1

| Compound | PGE$_2$[1] | PGE$_2$[2] | PGF$_2$[3] |
|---|---|---|---|
| 1 | 7.1 × 10$^{-6}$M(2×)[4] | 10 × 10$^{-6}$(5×) | 6.7 × 10$^{-6}$(5×) |
| 2 | 1.4 × 10$^{-6}$(3×) | | |
| 3 | No inhibition at 30 × 10$^{-6}$ | | |
| 4 | 12 × 10$^{-6}$(2×) | | |

[1]PGE$_2$: Guinea pig ileum IC$_{50}$ vs Prostaglandin E$_2$
[2]PGE$_2$: Rat fundus IC$_{50}$ vs Prostaglandin E$_2$
[3]PGF$_{2\alpha}$: Rat fundus IC$_{50}$ vs Prostaglandin F$_2$
[4]Refers to number of tests e.g. 2× is 2 tests.

It is apparent from the foregoing that compounds 1 and 2 are prostaglandin receptor blockers while compounds 3 and 4 are weak or have no prostaglandin-blocking activity.

Table 2

Compound 1 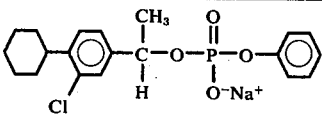

Compound 2 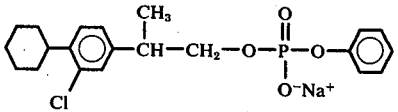

Compound 3 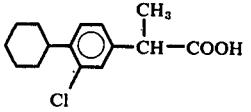

Compound 4 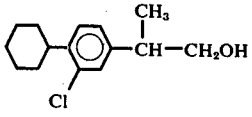

Compound 5 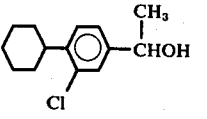

EXAMPLE IV

Compounds were tested for prostaglandin synthetase inhibition via the procedure of Flower et al. (Prostaglandins 4: 325, 1973). These data are tabulated below in Table 3. The structure of the numbered compounds is shown in Table 2.

Table 3

| Compound | PGE$_2$ |
|---|---|
| 1 | 18 μM |
| 2 | 50 μM |
| 3 | 2 – 4 μM |
| 4 | no inhibition at 50 μM |
| 5 | insignificant inhibition at 50 μM |
| indomethacin | 10 – 12 μM |

PGE$_2$: ID$_{50}$ vs Prostaglandin E$_2$; enzyme source was bovine seminal vesicles.

The foregoing indicates that compound 1 is an effective blocker of prostaglandin synthetase, comparable in effect to indomethacin, a widely used anti-inflammatory compound having prostaglandin synthetase inhibition.

EXAMPLE V

The following compounds were tested in the standard Tonelli anti-inflammatory animal test model for their effectiveness in preventing croton oil-induced rat ear edema. The data are tabulated in Table 4 below. The structures of the compounds are shown in Table 2.

Table 4

| Compound | % protection at | | |
|---|---|---|---|
| | 0.3% | 1.0% | 3.0% |
| 1 | 0.0 | 23.4 | 53.8 |
| 2 | 15.9 | 51.3 | 65.4 |
| hydrocortisone | 13.8 | 45.9 | 68.7 |

On the basis of the foregoing results, it is apparent that compounds 1 and 2 of the invention are approximately as potent as hydrocortisone in reducing the edema produced by croton oil.

EXAMPLE VI

Compounds 1 and 2 of Table 2 were tested for their effectiveness in preventing mouse diarrhea induced by intraperitoneal prostaglandin E$_2$ injection. The data are summarized below in Table 5:

Table 5

| Compound | Dose administered[1] (Mg/kg) | % prevention of diarrhea |
|---|---|---|
| 1 | 30 | 0 |
| | 60 | 60 |
| | 100 | 70 |
| 2 | 30 | 40 |
| | 60 | 50 |
| | 100 | 70 |

[1]dose administered i.p.

Both compounds 1 and 2 are active when administered intraperitoneally in that they have ED$_{50}$'s of approximately 60 mg/kg.

In addition to the salts of the active compounds described herein, the invention further provides for any conventional pharmaceutically acceptable salt.

We claim:

1. A compound having the structural formula

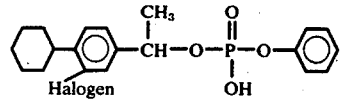

and a pharmaceutically acceptable salt thereof.

2. The compound of claim 1 wherein the halogen is chloro.

3. The compound of claim 1 wherein the salt is the sodium salt.

4. A compound having the structural formula

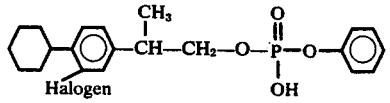

and a pharmaceutically acceptable salt thereof.

5. The compound of claim 4 wherein the halogen is chloro.

6. The compound of claim 4 wherein the salt is the sodium salt.

7. β-(3-chloro-4-cyclohexyl phenyl) propanol phenyl hydrogen phosphate monosodium salt.

8. α-(3-chloro-4-cyclohexyl phenyl) ethyl phenyl hydrogen phosphate monosodium salt.

* * * * *